(12) United States Patent
Grashow et al.

(10) Patent No.: US 11,638,795 B2
(45) Date of Patent: May 2, 2023

(54) SYSTEM AND METHOD FOR PROVIDING ENHANCED PAP METRICS

(71) Applicant: KONINKLIJKE PHILIPS N.V., Eindhoven (NL)

(72) Inventors: Jonathan Sayer Grashow, Pittsburgh, PA (US); Benjamin Irwin Shelly, Pittsburgh, PA (US); Michael Thomas Kane, Harrison City, PA (US); Gregory Delano Matthews, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 887 days.

(21) Appl. No.: 16/450,223

(22) Filed: Jun. 24, 2019

(65) Prior Publication Data

US 2020/0001030 A1    Jan. 2, 2020

Related U.S. Application Data

(60) Provisional application No. 62/691,945, filed on Jun. 29, 2018.

(51) Int. Cl.
*A61M 16/00* (2006.01)
*A61B 5/00* (2006.01)
(Continued)

(52) U.S. Cl.
CPC ....... *A61M 16/0069* (2014.02); *A61B 5/4815* (2013.01); *A61B 5/4818* (2013.01);
(Continued)

(58) Field of Classification Search
CPC ............ A61M 16/026; A61M 16/0066; A61M 16/0069; A61B 5/4815–4818;
(Continued)

(56) References Cited

U.S. PATENT DOCUMENTS 6,367,474 B1 *   4/2002   Berthon-Jones ...... A61M 16/06
                                                   128/204.26
8,523,758 B1 *   9/2013   Kirby ..................... A61M 21/02
                                                   600/26
(Continued)

FOREIGN PATENT DOCUMENTS

WO      2017122138 A1    7/2017
WO   WO-2017122138 A1 *  7/2017   ........... A61B 5/0205

OTHER PUBLICATIONS

International Search Report and Written Opinion, International Application No. PCT/EP2019/066736, dated Jan. 28, 2020.
(Continued)

*Primary Examiner* — Joseph D. Boecker
*Assistant Examiner* — Thomas W Greig

(57) ABSTRACT

A system for obtaining and providing enhanced PAP metrics of a patient's sleep period includes: a pressure support device for use in providing a flow of breathing gas to the patient; a processing unit; and a number of auxiliary devices in wireless communication with the processing unit. Each auxiliary device of the number of auxiliary devices is structured to detect and collect sleep-related data of the patient. The processing unit is programmed to: receive data obtained by a number of sensors of the pressure support device during operation of the pressure support device in providing the flow of breathing gas to the patient; receive
(Continued)

supplemental data obtained by the number of auxiliary devices while the pressure support device is not providing the flow of breathing gas to the patient; and determine the enhanced PAP metrics of the sleep period of the patient utilizing the data and the supplemental data.

20 Claims, 3 Drawing Sheets

(51) Int. Cl.
*A61M 16/06* (2006.01)
*A61M 16/08* (2006.01)

(52) U.S. Cl.
CPC ............ *A61B 5/681* (2013.01); *A61B 5/6892* (2013.01); *A61B 5/6898* (2013.01); *A61M 16/026* (2017.08); *A61M 16/06* (2013.01); *A61M 16/0875* (2013.01); *A61M 2205/3584* (2013.01); *A61M 2230/40* (2013.01)

(58) Field of Classification Search
CPC ........ A61B 5/681; A61B 5/6892–6898; A61B 5/0002; A61B 5/0015; A61B 5/002; A61B 5/0024; A61B 5/08; A61B 5/0803; A61B 5/0816; A61B 5/0823; A61B 5/082; A61B 5/0022

See application file for complete search history.

(56) References Cited

U.S. PATENT DOCUMENTS

| | | | |
|---|---|---|---|
| 9,533,114 B1* | 1/2017 | Kayyali | A61B 5/4818 |
| 10,055,549 B2* | 8/2018 | Chung | G16H 50/20 |
| 10,888,266 B2* | 1/2021 | Scarberry | A61B 5/318 |
| 2014/0088373 A1* | 3/2014 | Phillips | A61B 5/0507 |
| | | | 600/301 |
| 2015/0164375 A1* | 6/2015 | Schindhelm | G08B 21/02 |
| | | | 600/534 |
| 2016/0193437 A1* | 7/2016 | Bao | G16H 40/67 |
| | | | 128/203.14 |
| 2017/0071533 A1 | 3/2017 | Warren et al. | |

OTHER PUBLICATIONS

Penzel, T. et al., "New technology to assess sleep apnea: wearables, smartphones, and accessories", vol. 7, Jan. 2018.

* cited by examiner

SYSTEM AND METHOD FOR PROVIDING ENHANCED PAP METRICS

CROSS-REFERENCE TO PRIOR APPLICATIONS

This application claims the benefit of U.S. Patent Application No. 62/691,945, filed on 29 Jun. 2018. This application is hereby incorporated by reference herein.

BACKGROUND OF THE INVENTION

1. Field of the Invention

The present invention pertains methods for providing enhanced PAP metrics. The present invention also relates to systems for use in carrying out such methods.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing. Devices used in any of the aforementioned therapies may be generally referred to as positive airway pressure (PAP) devices.

Pressure support therapies as just described involve the placement of a patient interface device including a mask component having a soft, flexible sealing cushion on the face of the patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is typically secured to the patient's head by a headgear component. The patient interface device is connected to a gas delivery tube or conduit and interfaces the pressure support device with the airway of the patient, so that a flow of breathing gas can be delivered from the pressure/flow generating device to the airway of the patient.

Current PAP devices are capable of reporting metrics for the patient to the healthcare provide that reflect the amount of PAP usage (i.e., adherence) and the effectiveness of the therapy during sleep (e.g., the Apnea-Hypopnea Index (AHI)). However, metrics reported by current PAP devices only reflect the effectiveness of the treatment when the PAP device is in use, and thus may not provide a complete picture of a patient's sleep as the patient may not have the PAP device in operation at times while sleeping.

SUMMARY OF THE INVENTION

Accordingly, embodiments of the present invention improve upon existing systems and methods by providing a more complete picture of the patient's sleep which may be utilized by healthcare providers to improve treatment provided to the patient.

As one aspect of the invention, a system for obtaining and providing enhanced PAP metrics of a sleep period of a patient is provided. The system comprises: a pressure support device for use in providing a flow of breathing gas to the patient; a processing unit; and a number of auxiliary devices in wireless communication with the processing unit, each auxiliary device of the number of auxiliary devices being structured to detect and collect sleep-related data of the patient. The processing unit is programmed to: receive data obtained by a number of sensors of the pressure support device during operation of the pressure support device in providing the flow of breathing gas to the patient; receive supplemental data obtained by the number of auxiliary devices while the pressure support device is not providing the flow of breathing gas to the patient; and determine the enhanced PAP metrics of the sleep period of the patient utilizing the data and the supplemental data.

The processing unit may be a portion of the pressure support device.

The processing unit may be a portion of another device separate from the processing unit and the auxiliary devices.

The processing unit may be a portion of one of the number of auxiliary devices.

The number of auxiliary devices may comprise one or more of: a smart watch, a smart phone, a bedside sleep monitor, and an under-mattress-sensor.

The processing unit may be further programmed to communicate the enhanced PAP metrics of the sleep period to another device.

The number of auxiliary devices may comprise at least three devices, and the processing unit may be further programmed exclude data from one auxiliary device of the number of auxiliary devices which does not correspond to data from the other auxiliary device of the number of auxiliary devices.

The processing unit may be further programmed to utilize the enhanced PAP metrics to determine and implement adjustments to the treatment provided to the patient by the pressure support device.

As another aspect of the invention, a method for providing enhanced PAP metrics of a sleep period of a patient is provided. The sleep period having a first portion during which the patient receives treatment from a pressure support device and a second portion in which the patient does not receive treatment from the pressure support device. The method comprises: receiving data obtained during the first portion of the sleep period by a number of sensors of the pressure support device; receiving supplemental data obtained during the second portion of the sleep period by a number of auxiliary devices; and determining enhanced PAP metrics of the patient's entire sleep period utilizing the data and the supplemental data.

The method may further comprise communicating the enhanced PAP metrics.

The method may further comprise analyzing the enhanced PAP metrics and adjusting the treatment given to the patient by the pressure support device.

As yet another aspect of the invention, a method for providing enhanced PAP metrics of a sleep period of a patient is provided. The sleep period having a first portion during which the patient receives treatment from a pressure support device and a second portion in which the patient does not receive treatment from the pressure support device. The method comprises: receiving data obtained during the first portion of the sleep period by a number of sensors of the pressure support device; receiving supplemental data obtained during first portion of the sleep period by a number of auxiliary devices; determining the occurrence of one or more SDB events during the first portion of the sleep period from one or both of the data and the supplemental data; identifying a correlation between the SDB events detected by the number of sensors of the pressure support device and the number of auxiliary devices; receiving supplemental data obtained during second portion of the sleep period by a number of auxiliary devices; and determining enhanced PAP metrics of the patient's entire sleep period utilizing the data obtained during the first portion of the sleep period and the correlation with the supplemental data obtained during the second portion of the sleep period.

The method may further comprise communicating the enhanced PAP metrics.

The method may further comprise utilizing the enhanced PAP metrics to adjust the treatment provided to the patient by the pressure support device.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
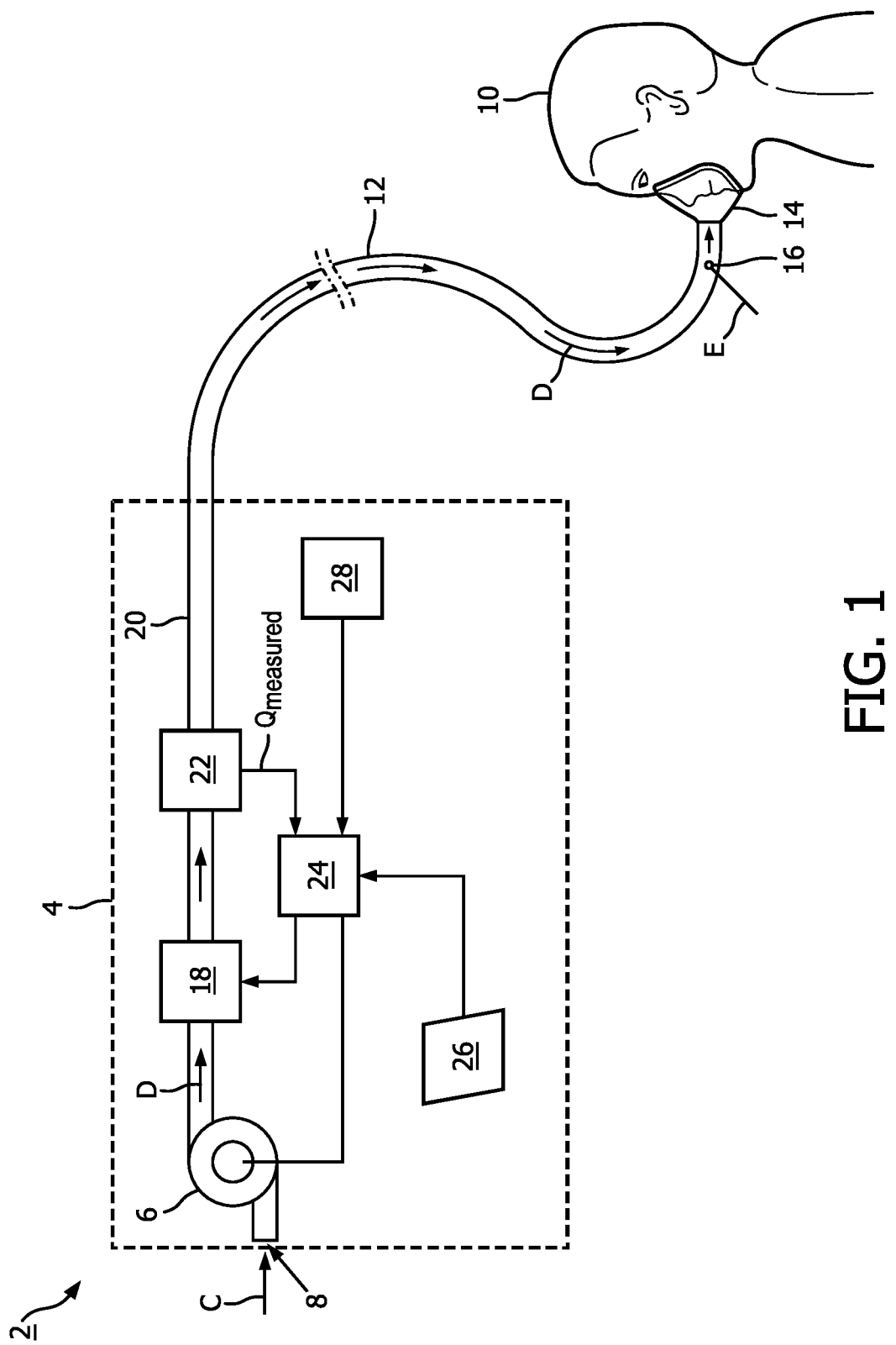
FIG. 1 is a partially schematic view of an airway pressure support system including a pressure generating device in accordance with one example embodiment of the present invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

As used herein, the singular form of "a", "an", and "the" include plural references unless the context clearly dictates otherwise. As used herein, "and/or" shall mean one or both of the elements which are separated by such phrase (e.g., A and/or B would mean A, B, or both of A and B). As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to maintain a constant, fixed orientation relative to each other. As used herein, "selectively coupled" means that two components are coupled in a manner which allows for the components to be readily coupled or uncoupled in a predictable, repeatable manner without damaging either of the components. Unless particularly described otherwise herein, any components which are described merely as being "coupled", may also be "fixedly" or "selectively" coupled without varying from the scope of the present invention.

As used herein, the word "unitary" means a component is created as a single piece or unit. That is, a component that includes pieces that are created separately and then coupled together as a unit is not a "unitary" component or body. As used herein, the statement that two or more parts or components "engage" one another shall mean that the parts exert a force against one another either directly or through one or more intermediate parts or components. As used herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

An example airway pressure support system 2 which may be employed as a portion of one particular, non-limiting exemplary embodiment of the present invention is shown in FIG. 1. Airway pressure support system 2 includes a pressure support device 4 which houses a blower assembly 6, an example of which will be described in further detail below. Blower assembly 6 receives breathing gas, generally indicated by arrow C, from the ambient atmosphere through a filtered air inlet 8 provided as part of pressure support device 4, and generates a flow of breathing gas therefrom for delivery to an airway of a patient 10 at relatively higher and lower pressures, i.e., generally equal to or above ambient atmospheric pressure, to generate pressure to provide pressure compensation to patient 10 via a patient circuit 12,14. In the exemplary embodiment, blower assembly 6 is capable of providing a flow of breathing gas ranging in pressure from 2-30 cmH2O. The pressurized flow of breathing gas from blower assembly 6, generally indicated by arrow D, is delivered via a delivery conduit 12 to a breathing mask or patient interface 14 of any known construction, which is typically worn by or otherwise attached to patient 10 to communicate the flow of breathing gas to the airway of patient 10. Delivery conduit 12 and patient interface device 14 are typically collectively referred to as the patient circuit.

Pressure support system 2 shown in FIG. 1 is what is known as a single-limb system, meaning that the patient circuit includes only delivery conduit 12 connecting patient 10 to pressure support system 2. As such, an exhaust vent 16 is provided in delivery conduit 12 for venting exhaled gases from the system as indicated by arrow E. It should be noted that exhaust vent 16 can be provided at other locations in addition to or instead of in delivery conduit 12, such as in patient interface device 14. It should also be understood that exhaust vent 16 can have a wide variety of configurations depending on the desired manner in which gas is to be vented from pressure support system 2.

The present concept also contemplates that pressure support system 2 can be a two-limb system, having a delivery conduit and an exhaust conduit connected to patient 10. In a two-limb system (also referred to as a dual-limb system), the exhaust conduit carries exhaust gas from patient 10 and includes an exhaust valve at the end distal from patient 10. The exhaust valve in such an embodiment is typically actively controlled to maintain a desired level or pressure in the system, which is commonly known as positive end expiratory pressure (PEEP).

Furthermore, in the illustrated exemplary embodiment shown in FIG. 1, patient interface 14 is a nasal/oral mask. It is to be understood, however, that patient interface 14 can include a nasal mask, nasal pillows, a tracheal tube, an endotracheal tube, or any other device that provides a suitable gas flow communicating function. Also, for purposes of the present invention, the phrase "patient interface" can include delivery conduit 12 and any other structures that couple the source of pressurized breathing gas to patient 10.

In the illustrated embodiment, pressure support system 2 includes a pressure controller in the form of a valve 18 provided in internal delivery conduit 20 provided in a housing of pressure support device 4. Valve 18 controls the pressure of the flow of breathing gas from blower assembly 6 that is delivered to patient 10. For present purposes, blower assembly 6 and valve 18 are collectively referred to as a pressure generating system because they act in concert to generate and control the pressure and/or flow of gas delivered to patient 10. However, it should be apparent that other techniques for controlling the pressure of the gas delivered to patient 10, such as varying the speed of blower assembly 6, either alone or in combination with a pressure control valve, are contemplated by the present invention. Thus, valve 18 is optional depending on the technique used to control the pressure of the flow of breathing gas delivered to patient 10. If valve 18 is eliminated, the pressure generating system corresponds to blower assembly 6 alone, and the pressure of gas in the patient circuit is controlled, for example, by controlling the speed of blower assembly 6.

Pressure support system 2 further includes a flow sensor 22 that measures the flow of the breathing gas within delivery conduit 20 and delivery conduit 12. In the particular embodiment shown in FIG. 1, flow sensor 22 is interposed in line with delivery conduits 20 and 12, most preferably downstream of valve 18. Pressure support system 2 additionally includes a pressure sensor 28 that detects the pressure of the pressurized fluid in delivery conduit 20. While the point at which the flow is measured by flow sensor 22 and the pressure is measured by pressure sensor 28 are illustrated as being within pressure support device 4, it is to be understood that the location at which the actual flow and pressure measurements are taken may be anywhere along delivery conduits 20 or 12. The flow of breathing gas measured by flow sensor 22 and the pressure detected by pressure sensor 28 are provided to a processing unit 24 to determine the flow of gas at patient 10 ($Q_{PATIENT}$).

Processing unit 24 includes a processing portion which may be, for example, a microprocessor, a microcontroller or some other suitable processing device, and a memory portion that may be internal to the processing portion or operatively coupled to the processing portion and that provides a storage medium for data and software executable by the processing portion for controlling the operation of pressure support system 2. Processing unit 24 is structured to receive outputs of one or more sensors, such as those previously discussed, which are structured to gather data related to effectiveness of the pressure support therapy. Processing unit 24 is also structured to analyze outputs of the sensors while pressure support therapy is provided to the patient to determine patient airflow and pressure waveforms in the patient circuit.

An input/output device 26 is provided for setting various parameters used by pressure support system 2, as well as for displaying and outputting information and data to a user, such as a clinician or caregiver.

Figure 2:
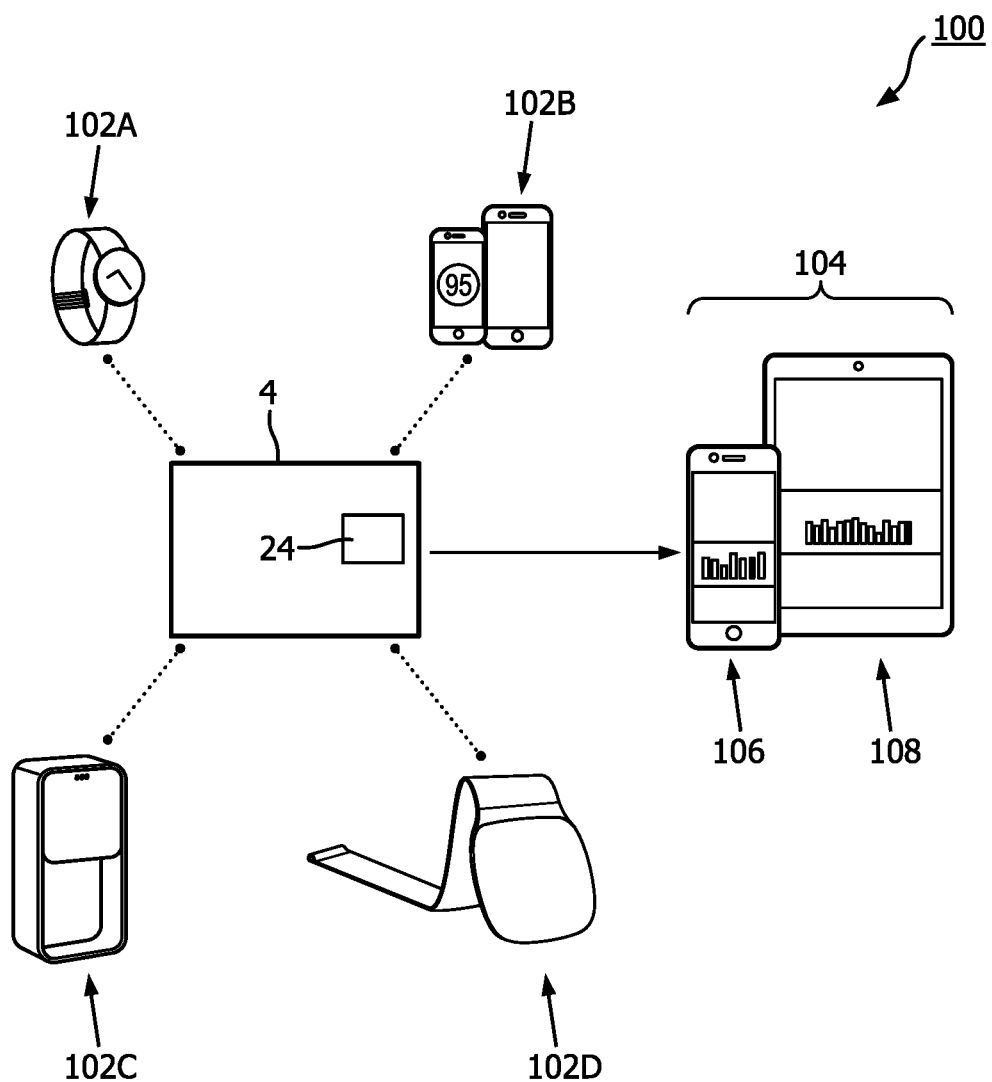
FIGS. 2 and 3 are partially schematic views of systems for use in carrying out methods in accordance with example embodiments of the present invention.

A system 100 for use in carrying out a method for providing enhanced PAP metrics of a patient (not shown) in accordance with one example embodiment of the present invention is shown, partially schematically, in FIG. 2. System 100 includes a pressure support device, such as pressure support device 4, previously described in FIG. 1, having processing unit 24. System 100 further includes a number (four are shown in the example) of auxiliary devices 102A, 102B, 102C, 102D which are structured to detect and collect sleep-related data and are each in wireless communication (e.g., via Bluetooth) with pressure support device 4 and processing unit 24 thereof. More particularly, the number of auxiliary devices includes a smart watch 102A, a smart phone 102B, a bedside sleep monitor 102C, and an under-mattress-sensor 102D. Smart watch 102A, which is structured to be worn by the patient, is structured to detect one or both of heart rate and actigraphy of the patient and wirelessly communicate data related thereto to processing unit 24. Smart phone 102B includes sensors which are structured to monitor breathing and other sounds of the patient and wirelessly communicate data related thereto to processing unit 24. Additionally, smart phone 102B may be employed to monitor bed vibrations and wirelessly communicate data related thereto to processing unit 24. Bedside sleep monitor 102C provides non-contact sensing of the patient's breathing and body movements and wirelessly communicates data related thereto to processing unit 24. Under mattress sensor 102D includes sensors which are structured to detect the patient's heart rate, respiratory rate, and movement and wirelessly communicate data related thereto to processing unit 24. It is to be appreciated that although four example auxiliary devices 102A-102D are employed in system 100, the quantity and/or type of such devices may be varied (devices other than those shown may be employed, e.g., without limitation, an SpO2 sensor) without varying from the scope of the present invention.

Similar to existing pressure support devices, processing unit 24 is programmed to utilize sensors (e.g., flow sensor 22, pressure sensor 28) within pressure support device 4 to summarize sleep quality (e.g., sleep disordered breathing events) of the patient when pressure support device 24 is in use by the patient. Unlike existing arrangements which do not record or analyze anything when the pressure support device is not being used by a patient, processing unit 24 is further programmed to receive and analyze supplemental data from one or more of the number of auxiliary devices 102A-102D and use such data to measure (or estimate) sleep quality of the patient when pressure support device 4 is not in use, but sleep is detected by one or more of auxiliary devices 102A-102D. Processing unit 24 is further programmed to utilize such supplemental data in addition to the data collected when pressure support device 4 was in use to create "total night" sleep quality metrics that reflect sleep quality of the patient for periods of the night when pressure support device 4 was in use as well as periods of the night when pressure support device 24 was not in use. It is to be appreciated that since auxiliary devices 102A-102D may not have the respiratory sensory required to directly detect SDB events, the combined metrics may be more general sleep quality metrics (e.g. actigraphy indicating poor sleep). Such "total night" sleep quality metrics can then be communicated (via, local wireless, cellular, internet, or any suitable arrangement) to a remote electronic device or devices 104 (e.g., smart phone 106, tablet 108, or any other suitable electronic device) for further review by a physician or caregiver.

Figure 3:
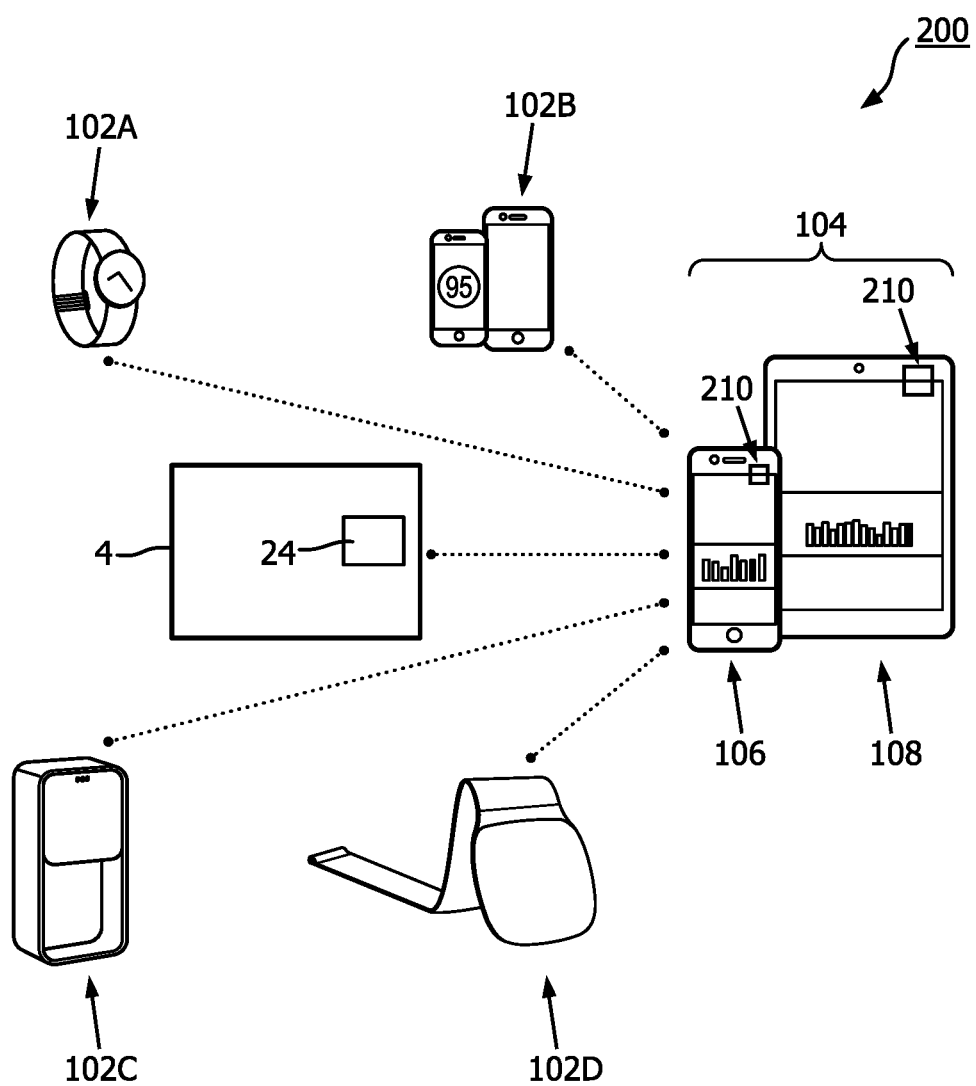

A system 200 for use in carrying out a method for providing enhanced PAP metrics of a patient (not shown) in accordance with another example embodiment of the present invention is shown, partially schematically, in FIG. 3. System 200 includes generally the same components as system 100 which function in a similar manner as in system 200 with generally one notable exception. Instead of auxiliary components 102A-102D communicating with processing unit 24 of pressure support device 4, auxiliary components 102A-102D, as well as processing unit 24, wirelessly communicate (e.g., via any suitable local or distant arrangement) either directly or indirectly (e.g., via local wireless and internet) with a remote processing unit 210, which may be a portion of remote electronic device 104 (e.g., smart phone 106 or tablet 108) such as shown in FIG. 3, which may be located on a cloud-based server, or any other suitable location. Remote processing unit 210 is programmed in a similar manner as processing unit 24 to create "total night" sleep quality metrics that reflect sleep quality of the patient for periods of the night when pressure support device 4 was in use as well as periods of the night when pressure support device 24 was not in use.

In an alternate embodiment, the start and stop times of pressure support device 4 (i.e. when the patient started therapy and when the patient took off the mask or turned off the CPAP) could be used to segment the reporting of sleep quality-related data from data provided by auxiliary devices 102A-102D. As an example, in the morning the sleep therapy system could summarize actigraphy data from a smart watch separately for periods of the night in which the PAP was in use and those periods when the PAP was not in use in order to highlight how much more restful the patients sleep was (less movement) when the PAP was in use.

When multiple auxiliary devices are utilized, such as in systems 100 or 200, a cross-checking protocol may be employed to exclude erroneous measurements. For example, if four auxiliary devices are connected and one of the devices detects an apnea, but the other three do not, the detected event may be excluded from the total night summary as being most likely an erroneous detection.

Systems such as described herein may also include a "calibration mode" which concurrently collects data from a pressure support device and connected auxiliary devices in order to identify correlations between SDB events detected by the pressure support device and auxiliary data. Such calibration allows the sleep therapy system to better estimate SDB events when PAP is not in use (after calibration period is complete).

In example embodiments of the invention, when one connected auxiliary device malfunctions or becomes disconnected from the system, data for the malfunctioning device can be estimated using trends in other system data (e.g. PAP sensor data or data from other auxiliary devices) in order to "fill in any holes" in the data. As an example, if data from one connected auxiliary device is not available for 2 days, but all other data looks "normal" then the missing data can be estimated using previously collected "normal" data from the malfunctioning device.

From the foregoing it is thus to be appreciated that embodiments of the present invention provide a more complete analysis of a patient's sleep which can be employed by a physician or other caregiver to improve a patient's treatment.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. A system for obtaining and providing enhanced PAP metrics of a sleep period of a patient, the system comprising:
a pressure support device for use in providing a flow of breathing gas to the patient;
a processing unit; and
a number of auxiliary devices in wireless communication with the processing unit, each auxiliary device of the number of auxiliary devices being structured to detect and collect sleep-related data of the patient,
wherein the processing unit is programmed to:
receive data obtained by a number of sensors of the pressure support device during operation of the pressure support device in providing the flow of breathing gas to the patient while the patient sleeps;
receive supplemental data obtained by the number of auxiliary devices while the pressure support device is not providing the flow of breathing gas to the patient, wherein the supplemental data comprises sleep-related data of the patient that is detected and collected during periods of time in which the pressure support device provides no flow of breathing gas to the patient while the patient sleeps; and
determine the enhanced PAP metrics of the sleep period of the patient utilizing a combination of both the data and the supplemental data, wherein the enhanced PAP metrics comprise metrics that reflect a total sleep quality of the patient's sleep period in comparison to PAP metrics of the patient's sleep period that are determined utilizing the data alone.

2. The system of claim 1, wherein the processing unit comprises a processing unit of the pressure support device.

3. The system of claim 1, wherein the processing unit comprises a processing unit of another device separate from the pressure support device and the auxiliary devices.

4. The system of claim 1, wherein the processing unit comprises a processing unit of one of the number of auxiliary devices.

5. The system of claim 1, wherein the number of auxiliary devices comprises one or more of: a smart watch, a smart phone, a bedside sleep monitor, and an under-mattress-sensor.

6. The system of claim 1, wherein the processing unit is further programmed to communicate the enhanced PAP metrics of the sleep period to another device.

7. The system of claim 1, wherein the number of auxiliary devices comprises at least three devices, and wherein the processing unit is further programmed to exclude data from one auxiliary device of the number of auxiliary devices which does not correspond to data from the other auxiliary devices of the number of auxiliary devices.

8. The system of claim 1, wherein the processing unit is further programmed to utilize the enhanced PAP metrics to determine and implement adjustments to the treatment provided to the patient by the pressure support device.

9. A method for obtaining and providing enhanced PAP metrics of a sleep period of a patient, the sleep period having (i) a first portion during which the patient receives a flow of breathing gas from a pressure support device while the patient sleeps and (ii) a second portion in which the the pressure support device provides no flow of breathing gas to the patient while the patient sleeps, the method comprising:
receiving, via a processing unit, data obtained during the first portion of the sleep period by a number of sensors of the pressure support device;
receiving, via the processing unit, supplemental data obtained during the second portion of the sleep period by a number of auxiliary devices, wherein the supplemental data comprises sleep-related data of the patient that is detected and collected during the second portion of the sleep period in which the pressure support device provides no flow of breathing gas to the patient while the patient sleeps; and
determining, via the processing unit, enhanced PAP metrics of the patient's entire sleep period utilizing a combination of both the data and the supplemental data, wherein the enhanced PAP metrics comprise metrics that reflect a total sleep quality of the patient's sleep period in comparison to PAP metrics of the patient's sleep period that are determined utilizing the data alone.

10. The method of claim 9, further comprising communicating, via the processing unit, the enhanced PAP metrics of the sleep period to a device other than the pressure support device and the auxiliary devices.

11. The method of claim 9, further comprising utilizing, via the processing unit, the enhanced PAP metrics to determine and implement adjustments to a treatment provided to the patient by the pressure support device.

12. The method of claim 9, wherein the processing unit comprises one selected from the group consisting of (i) a processing unit of the pressure support device, (ii) a processing unit of one of the number of auxiliary devices, and (iii) a processing unit of another device separate from the pressure support device and the auxiliary devices.

13. The method of claim 9, wherein the number of auxiliary devices comprises one or more of: a smart watch, a smart phone, a bedside sleep monitor, and an under-mattress-sensor.

14. The method of claim 9, wherein the number of auxiliary devices comprises at least three devices, the method further comprising:
excluding, via the processing unit, supplemental data from one auxiliary device of the number of auxiliary devices which does not correspond to supplemental data from the other auxiliary devices of the number of auxiliary devices.

15. A method for providing enhanced PAP metrics of a sleep period of a patient, the sleep period having (i) a first portion during which the patient receives a flow of breathing gas from a pressure support device while the patient sleeps and (ii) a second portion in which the pressure support device provides no flow of breathing gas to the patient while the patient sleeps, the method comprising:
receiving, via a processing unit, data obtained during the first portion of the sleep period by a number of sensors of the pressure support device;
receiving, via the processing unit, first supplemental data obtained during first portion of the sleep period by a number of auxiliary devices, wherein the first supplemental data comprises sleep-related data of the patient that is detected and collected during the first portion of the sleep period in which the patient receives the flow of breathing gas while the patient sleeps;
determining, via the processing unit, the occurrence of one or more SDB events during the first portion of the sleep period from one or both of the data and the first supplemental data;

identifying, via the processing unit, a correlation between the SDB events detected by (i) the number of sensors of the pressure support device and (ii) the number of auxiliary devices;

receiving, via the processing unit, second supplemental data obtained during second portion of the sleep period by a number of auxiliary devices, wherein the second supplemental data comprises sleep-related data of the patient that is detected and collected during the second portion of the sleep period in which the pressure support device provides no flow of breathing gas to the patient while the patient sleeps; and determining, via the processing unit, enhanced PAP metrics of the patient's entire sleep period utilizing a combination of (i) both the data and first supplemental data obtained during the first portion of the sleep period, (ii) the correlation, and (iii) the second supplemental data obtained during the second portion of the sleep period, wherein the enhanced PAP metrics comprise metrics that reflect a total sleep quality of the patient's sleep period in comparison to PAP metrics of the patient's sleep period that are determined utilizing the data alone.

16. The method of claim 15, further comprising communicating, via the processing unit, the enhanced PAP metrics of the sleep period to a device other than the pressure support device and the auxiliary devices.

17. The method of claim 15, further comprising utilizing, via the processor, the enhanced PAP metrics to determine and implement adjustments to a treatment provided to the patient by the pressure support device.

18. The method of claim 15, wherein the processing unit comprises one selected from the group consisting of (i) a processing unit of the pressure support device, (ii) a processing unit of one of the number of auxiliary devices, and (iii) a processing unit of another device separate from the pressure support device and the auxiliary devices.

19. The method of claim 15, wherein the number of auxiliary devices comprises one or more of: a smart watch, a smart phone, a bedside sleep monitor, and an under-mattress-sensor.

20. The method of claim 15, wherein the number of auxiliary devices comprises at least three devices, the method further comprising:

excluding, via the processing unit, first and second supplemental data from one auxiliary device of the number of auxiliary devices which does not correspond to respective first and second supplemental data from the other auxiliary devices of the number of auxiliary devices.

* * * * *